United States Patent
Linares

(10) Patent No.: US 9,050,193 B2
(45) Date of Patent: Jun. 9, 2015

(54) ARTIFICIAL WEAR RESISTANT PLUG FOR MOUNTING TO EXISTING JOINT BONE

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

(21) Appl. No.: 14/258,544

(22) Filed: Apr. 22, 2014

(65) Prior Publication Data

US 2014/0228962 A1   Aug. 14, 2014

Related U.S. Application Data

(62) Division of application No. 12/919,242, filed as application No. PCT/US2009/041627 on Apr. 24, 2009, now Pat. No. 8,702,801.

(60) Provisional application No. 61/031,192, filed on Feb. 25, 2008.

(51) Int. Cl.
*A61F 2/38* (2006.01)
*A61F 2/30* (2006.01)

(52) U.S. Cl.
CPC ......... *A61F 2/38* (2013.01); *A61F 2002/30281* (2013.01); *A61F 2002/30405* (2013.01); *A61F 2002/30604* (2013.01); *A61F 2/30756* (2013.01); *A61F 2/30965* (2013.01); *A61F 2/3854* (2013.01); *A61F 2/3872* (2013.01); *A61F 2002/30069* (2013.01);

(Continued)

(58) Field of Classification Search
CPC ............ A61F 2/38; A61F 2002/30069; A61F 2002/3028; A61F 2002/30281
USPC ...................... 623/18.11, 17.11, 17.14, 17.15, 623/19.11–19.14, 20.14–20.36, 623/21.11–21.13, 21.15–21.19, 23, 39, 623/23.4, 23.44
See application file for complete search history.

(56) References Cited

U.S. PATENT DOCUMENTS

| 2,667,644 A | 2/1954 | Johnson |
| 3,651,521 A | 3/1972 | Devas |

(Continued)

FOREIGN PATENT DOCUMENTS

JP     7116184     9/1995

OTHER PUBLICATIONS

International Search Report—International application No. PCT/US2011/042624.

*Primary Examiner* — Marcia Watkins
(74) *Attorney, Agent, or Firm* — Gifford, Krass, Sprinkle, Anderson & Citkowski, P.C.; Douglas J. McEvoy

(57) ABSTRACT

An artificial and wear-resistant plug mounted to an existing bone associated with a joint structure and which includes a three dimensional and composite plasticized material. An end surface of an existing bone is reconditioned in preparation for engagement of the plug thereto and in order to define a reconditioned artificial wear surface. In a preferred application, a pair end mounted plugs are arranged in opposing fashion between first and second bones and respectively define a male receiving end and a female socket. A lubricant retaining and cartilage defining exterior layer is applied to one or both of opposing surfaces of the plugs.

1 Claim, 4 Drawing Sheets

(52) U.S. Cl.
CPC ............... *A61F 2002/30433* (2013.01); *A61F 2002/30448* (2013.01); *A61F 2002/30673* (2013.01); *A61F 2002/30878* (2013.01); *A61F 2002/30886* (2013.01); *A61F 2002/3093* (2013.01); *A61F 2002/30937* (2013.01); *A61F 2002/3895* (2013.01); *A61F 2220/0041* (2013.01); *A61F 2220/005* (2013.01); *A61F 2240/001* (2013.01)

(56) References Cited

U.S. PATENT DOCUMENTS

| | | |
|---|---|---|
| 3,798,679 A | 3/1974 | Ewald |
| 3,875,594 A | 4/1975 | Swanson |
| 3,964,106 A | 6/1976 | Hutter, Jr. et al. |
| 4,215,439 A | 8/1980 | Gold et al. |
| 4,231,122 A | 11/1980 | Koeneman |
| 4,328,593 A | 5/1982 | Sutter et al. |
| 4,367,562 A | 1/1983 | Gauthier et al. |
| 4,538,305 A | 9/1985 | Engelbrecht et al. |
| 4,714,477 A | 12/1987 | Fichera et al. |
| 4,911,721 A * | 3/1990 | Bränemark et al. ......... 623/20.3 |
| 4,950,298 A | 8/1990 | Gustilo et al. |
| 4,964,868 A | 10/1990 | Bloebaum |
| 4,990,161 A | 2/1991 | Kampner |
| 5,007,934 A | 4/1991 | Stone |
| 5,021,061 A | 6/1991 | Wevers et al. |
| 5,092,898 A | 3/1992 | Bekki et al. |
| 5,123,928 A * | 6/1992 | Moser et al. ............... 623/20.24 |
| 5,171,325 A | 12/1992 | Aulie |
| 5,197,987 A | 3/1993 | Koch et al. |
| 5,389,107 A | 2/1995 | Nassar et al. |
| 5,462,362 A | 10/1995 | Yuhta et al. |
| 5,509,934 A | 4/1996 | Cohen |
| 5,553,476 A | 9/1996 | Oehy et al. |
| 5,571,193 A | 11/1996 | Kampner |
| 5,593,445 A | 1/1997 | Waits |
| 5,645,601 A | 7/1997 | Pope et al. |
| 5,662,158 A | 9/1997 | Caldarise |
| 5,676,702 A | 10/1997 | Ratron et al. |
| 5,702,476 A | 12/1997 | Limacher et al. |
| 5,728,175 A | 3/1998 | Rincoe |
| 5,800,566 A | 9/1998 | Gramnas et al. |
| 5,879,406 A | 3/1999 | Lilley |
| 5,916,269 A | 6/1999 | Serbousek et al. |
| 5,921,358 A | 7/1999 | Gramnas et al. |
| 6,045,581 A | 4/2000 | Burkinshaw |
| 6,165,223 A | 12/2000 | Metzger et al. |
| 6,398,815 B1 | 6/2002 | Pope et al. |
| 6,627,141 B2 | 9/2003 | McNulty et al. |
| 6,660,040 B2 | 12/2003 | Chan et al. |
| 6,692,679 B1 | 2/2004 | McNulty et al. |
| 6,723,102 B2 | 4/2004 | Johnson et al. |
| 6,800,298 B1 | 10/2004 | Burdick et al. |
| 6,800,670 B2 | 10/2004 | Shen et al. |
| 6,811,568 B2 | 11/2004 | Minamikawa |
| 6,818,172 B2 | 11/2004 | King et al. |
| 6,866,683 B2 | 3/2005 | Gerbec et al. |
| 6,866,685 B2 | 3/2005 | Chan et al. |
| 6,962,607 B2 | 11/2005 | Gundlapalli et al. |
| 7,044,983 B1 | 5/2006 | Cheng et al. |
| 7,066,958 B2 | 6/2006 | Ferree |
| 7,077,867 B1 | 7/2006 | Pope et al. |
| 7,087,091 B1 | 8/2006 | Chen et al. |
| 7,109,181 B2 | 9/2006 | Cowlen et al. |
| 7,148,209 B2 | 12/2006 | Hoemann et al. |
| 7,175,666 B2 | 2/2007 | Yao |
| 7,179,298 B2 | 2/2007 | Greenlee |
| 7,186,364 B2 | 3/2007 | King et al. |
| 7,331,995 B2 | 2/2008 | Eisermann et al. |
| 7,384,430 B2 | 6/2008 | Greer et al. |
| 7,578,851 B2 | 8/2009 | Dong et al. |
| 7,771,485 B2 | 8/2010 | Grundei |
| 7,780,738 B2 | 8/2010 | Khandkar et al. |
| 2002/0183845 A1 | 12/2002 | Mansmann |
| 2003/0055508 A1 | 3/2003 | Metzger et al. |
| 2003/0065401 A1 | 4/2003 | Amrich et al. |
| 2003/0114935 A1 | 6/2003 | Chan et al. |
| 2003/0208280 A1 * | 11/2003 | Tohidi et al. ............... 623/23.39 |
| 2003/0216669 A1 | 11/2003 | Lang et al. |
| 2004/0024460 A1 | 2/2004 | Ferree |
| 2004/0068322 A1 | 4/2004 | Ferree |
| 2005/0055100 A1 | 3/2005 | Lewis et al. |
| 2005/0171604 A1 | 8/2005 | Michalow |
| 2005/0192672 A1 | 9/2005 | Wyss et al. |
| 2005/0192674 A1 | 9/2005 | Ferree |
| 2005/0287187 A1 | 12/2005 | Mansmann |
| 2006/0015186 A1 | 1/2006 | Isaac |
| 2007/0179613 A1 | 8/2007 | Heinz |
| 2007/0255412 A1 * | 11/2007 | Hajaj et al. ................. 623/17.11 |
| 2007/0287027 A1 | 12/2007 | Justin et al. |
| 2008/0033567 A1 | 2/2008 | Stchur |
| 2008/0288081 A1 | 11/2008 | Scrafton et al. |
| 2009/0076605 A1 | 3/2009 | Linares |
| 2009/0125108 A1 | 5/2009 | Linares |

* cited by examiner

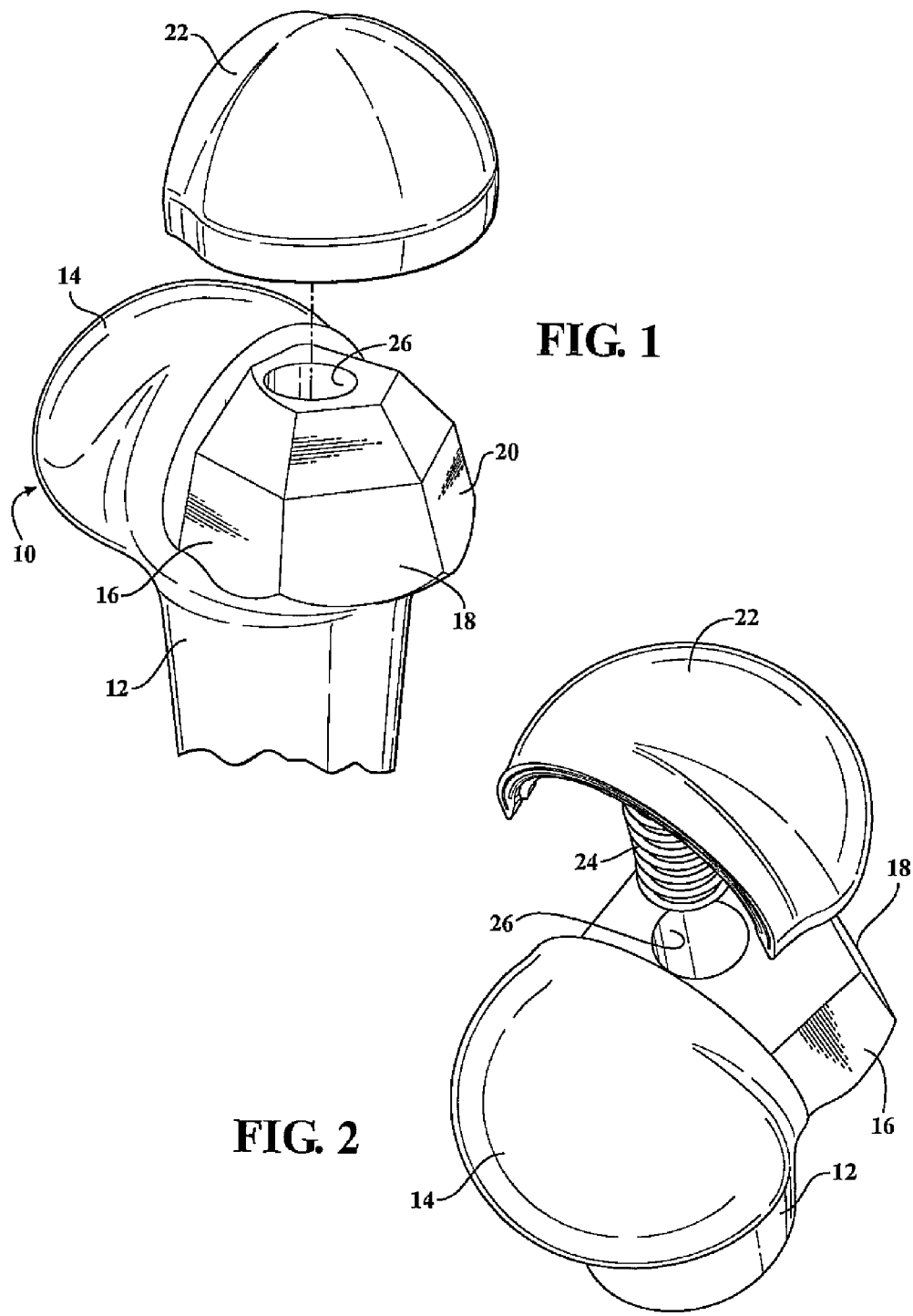

ARTIFICIAL WEAR RESISTANT PLUG FOR MOUNTING TO EXISTING JOINT BONE

CROSS-REFERENCE TO RELATED APPLICATIONS

This Application is a Division of application Ser. No. 12/919,242 filed on Aug. 25, 2010. Application PCT/US2009/041627, 014 and claims the benefit of U.S. Provisional Application 61/031,192 filed on Feb. 25, 2008. Application Ser. No. 12/919,242 now Issued U.S. Pat. No. 8,702,801, claims the benefit of U.S. Provisional Application 61/031,192 filed on Feb. 25, 2008, all contents of which are incorporated herein in their entirety.

FIELD OF THE INVENTION

The present invention relates generally to retrofit joint assemblies associated with existing bone structure. More specifically, the present invention discloses an artificial and wear-resistant plug adapted for mounting to an opposing end face of at least one existing and joint defined bone and in order to provide a retrofit knee assembly associated with reduce discomfort and recovery time.

BACKGROUND OF THE INVENTION

The prior art is documented with examples of implant devices and assemblies, such typically being retrofit applied to existing joints. Representative examples of known implant devices and assemblies include, among others, the implant device and method of manufacture set forth in Philipp, U.S. Publication No. 2008/0195216 and which teaches a knee implant with first and second component surfaces. U.S. Pat. No. 7,291,169, issued to Hodorek, teaches a cartilage implant for replacing a portion of the cartilage adjacent to a skeletal joint.

Additional examples of joint prosthesis include the implant of Buscheer, US 2008/0071381 which teaches an implant joint with a micro-rough bearing surface formed by sintering. Scott 2008/0114459 discloses a prosthesis implanted within a bone and including a shell and inter-fitting liner.

SUMMARY OF THE INVENTION

The present invention discloses an artificial and wear-resistant plug mounted to an existing bone associated with a joint structure and which includes a three dimensional and composite plasticized material. An end surface of an existing bone is reconditioned in preparation for engagement of the plug thereto and in order to define a reconditioned artificial wear surface. In a preferred application, a pair end mounted plugs are arranged in opposing fashion between first and second bones and respectively define a male receiving end and a female socket. A lubricant retaining and cartilage defining exterior layer is applied to one or both of opposing surfaces of the plugs.

Other features include a plurality of lubricant communicating channels associated with at least one of the plug and lubricant communicating layers. The polymeric insert plug further exhibits an integrally defined and interiorly extending root structure for being secured to a mating and associated interiorly machined surface of the bone. An injected expansion plastic is employed for filling a cavity established between said plug root structure and a cored recess of the bone.

At least one of the joint establishing and opposing implant plugs is secured through cutting, notching or abrasive resurfacing of an associated bone end surface prior to surface engagement thereto of at least one of the plasticized materials according to a specified shape and at a co-acting location with an opposing bone. The surface attached materials further can include clip portions which are secured to the bone end surfaces, via reverse face extending fasteners seating within interiorly machined drill hole locations associated with the bone ends.

In one variant, the plasticized insert material can include a miniaturized, flexible and depth-wise apertured wear disc placed in localized inter-disposed fashion between selected coacting surfaces associated with first and second joint establishing bone surface, the flexible wear disc further being constructed of a soft cushioning plastic. The composite plasticized material may also include a substantially keystone shaped insert configured for localized engagement with a selected joint end face location.

The insert may further exhibit under surface roughening such that, upon installing the insert into a machined end face of the bone in contact with the bone marrow, new bone adhesion is promoted. The composite plastic material may also incorporate a plastic insert with recess mounting studs, these securing at first and second abrading joint surface locations associated with the bone.

Additional variants include a whole or partial joint established between male projecting/extending and female/cup-shaped receiving end secured implants. The male and female defined ends are configured to mimic the normal interaction of surfaces corresponding to such as knee joint, as well as in additional applications to such as elbow and hip joints.

In addition to the male/female configured ends, the assembly may also include interconnecting/transitioning stem portions, these connecting at a first end to a rear surface of either male or female implant. The stem portions are interiorly hollowed with an open communicating end and are configured to seat within the hollow interior of the sectioned bone end. Surface area increasing portions, such as various types of keyed portions, are configured upon the open inner surfaces of the stem portions, these promoting the increase in natural bone growth and adhesion.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a perspective illustration of a male portion associated with a partial joint assembly according to an embodiment of the present invention;

FIG. 2 is a further rotated perspective of FIG. 1 and illustrating the threaded mounting shaft associated with the surface secured implant cap for adhesive engagement to a combined substrate and stem supporting portion;

DETAILED DESCRIPTION OF THE PREFERRED EMBODIMENTS

Figure 3:
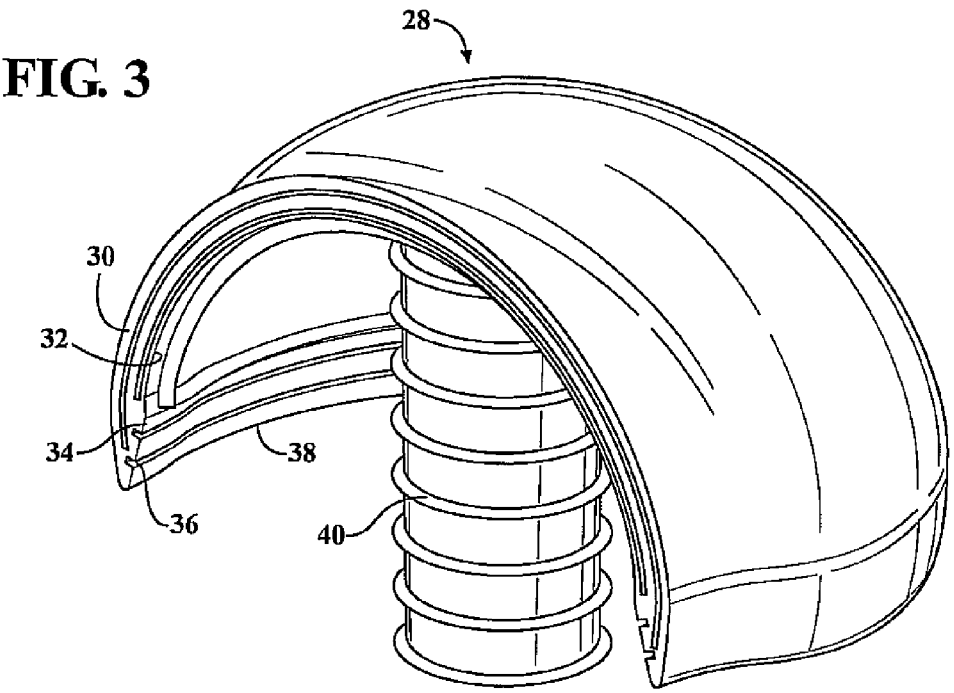
FIG. 3 is a further rotated perspective of the male implant supported cap shown in FIGS. 1 and 2.

Referring now to FIGS. 1-8 a series of illustrations are provided of a retrofit joint assembly according to various embodiments and which reconditions and repairs worn joints associated with natural bones. In particular, the present invention discloses associated articles, assemblies and methods for reconditioning, such as occurring in vivo within a patient and with the use of sophisticated medical drills and related tools, the worn ends of first and second bones and prior to installation of prosthetic joint implants which are much less invasive than previously known implant designs and which provide for dramatic increases in patient comfort and wear life.

Referring now to FIG. 1, a perspective illustration is shown at 10 of a male portion associated with a partial joint assembly according to a further preferred embodiment. In this variant, a stem shaped base component 12 incorporated into the reconditioned end of a selected bone can include an integral combination of a male implant body and bone securing stem. A further joint defining male convex portion, see at 14, can include an existing (and substantially undamaged) bone surface or can be provided as a further part of a prosthetic joint implant.

Alternatively, the stem can be separately mounted to the substrate portion of the male implant. It is also envisioned and understood that, alternative a bone secured implant, an actual bone end location can be reconditioned in order to exhibit the multi-sided and tapered configuration as illustrated by hex-shaped and interconnecting sides 16, 18, 20, et. seq.

As further shown in the rotated illustration of FIG. 2, a cap-shaped attachment, see at 22, includes a pseudo dome shaped (on convex shaped) top from which extends a threaded interior screw portion 24. The interior surface of the dome shaped top can exhibit a multi-sided configuration matching the pseudo hex shape designed into the implant 12, the screw portion 24 seating within an aperture 26 defined in a mating location of the base implant component 12. As previously described, adhesives or the like can be employed for securely bonding the cap attachment 22 to the base implant 12 and associated stem supporting portion.

Figure 4:
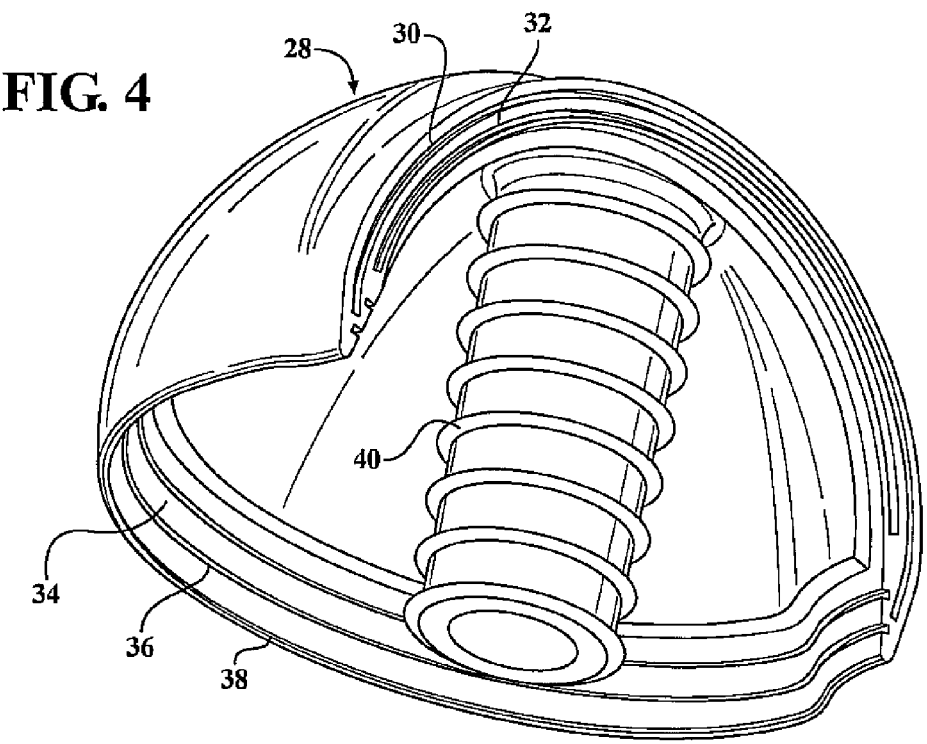
FIG. 4 is a yet further underside rotated perspective of the partial implant end cap shown in FIG. 3.

FIGS. 3 and 4 illustrate, generally at 28, first and second rotated perspectives of a further male implant cap attachment, such as similar to that shown in FIGS. 1 and 2. The cap attachment exhibits a reinforced construction, such as which can include the provision of stiffening and/or reinforcing inserts (see at 30 and 32) incorporated into the interior wall construction of the cap attachment and between inner and outer arcuate surfaces of the dome shaped cap attachment. The bottom extending inserts can also be removed in favor of recess notches to adjust the flexural nature of the cap attachment and it is also envisioned that the material construction of the component can be modified to exhibit different desired properties. Also illustrated are additional bottom positioned and inwardly/peripherally extending reinforcing inserts, at 34 and 36, these arranged proximate to a bottom extending edge 38 of the attachment cap. A threaded mounting screw 40 is again shown and to facilitate mounting of the cap to either an existing and reconditioned bone or a base supporting implant component as shown in FIG. 1.

Figures 5, 6:
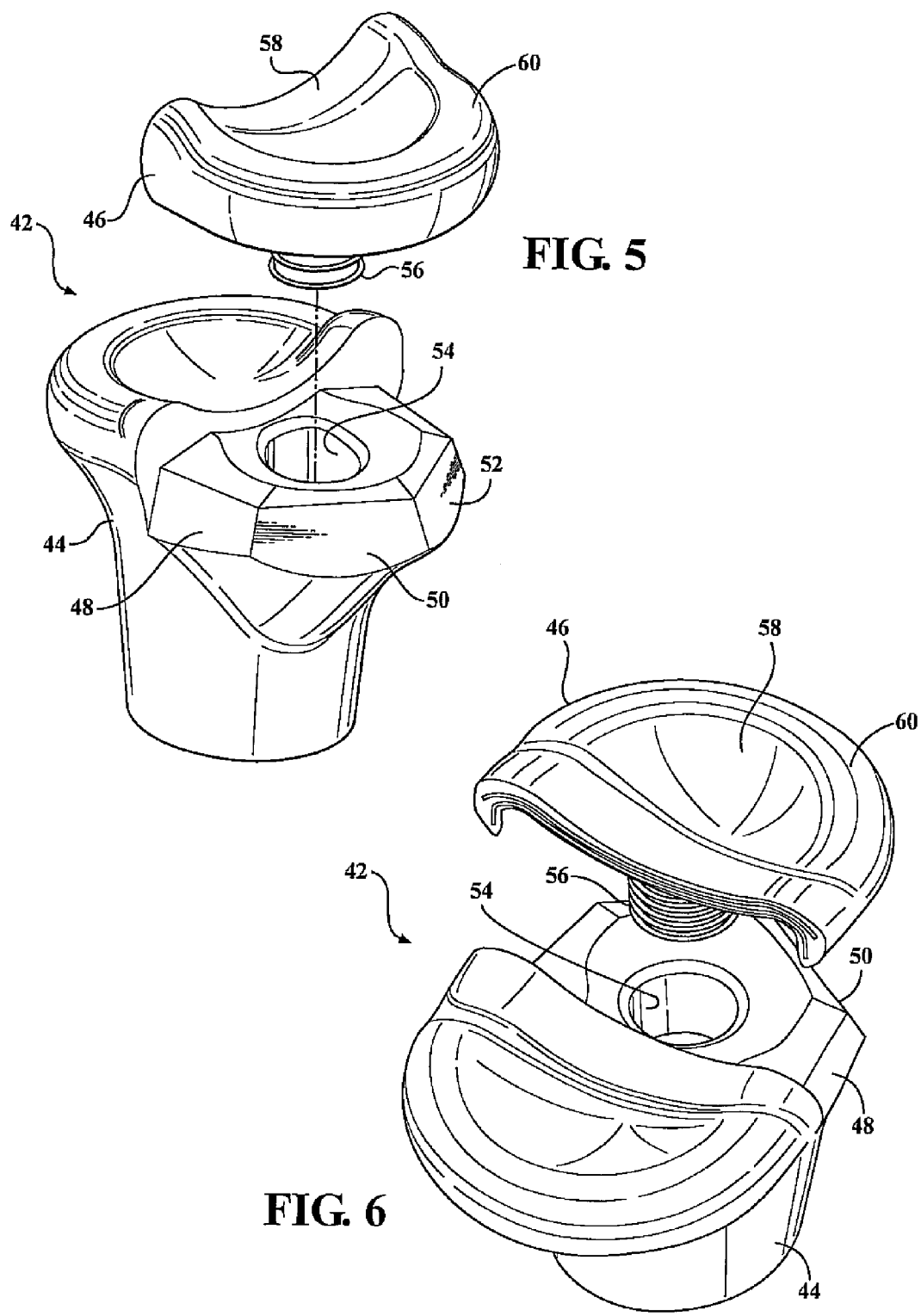
FIG. 5 is a perspective illustration of a female implant cap portion associated with a partial joint assembly, and such as which can be cooperatively established along with either a full or partial male implant assembly.
FIG. 6 is a rotated perspective of the female implant assembly of FIG. 5 and further showing a similar threaded mounting shaft for adhesive engagement with a recess defining location of a combined substrate and stem supporting portion of the female (or receiver) joint.

Referring to FIGS. 5 and 6, additional perspective illustrations are shown, generally at 42, of a further modified substrate joint assembly including a supporting stem 44 implanted within a reconditioned and joint defining bone end, and upon which is secured a configured female partial implant cap portion, further at 46, this associated with a partial joint assembly and such as which can be cooperatively established along with either a full or partial male implant assembly. The conditioning and mounting aspects illustrated are substantially identical as those described in relation to the male mounting arrangement shown in FIGS. 1 and 2, with a tapered hex pattern (sides 48, 50, 52, et. seq.) formed into an upper surface of a base component supported by the stem 44 and, along with an upper surface defined recess 54, seating and fixedly securing the female implant cap portion 46 and its associated and downwardly extending mounting screw portion 56.

The female cap shaped implant 46 otherwise exhibits a concave shaped top recess configuration 58 or depression bounded by a protruding outer ridge 60 this cooperatively seating the convex shape associated with the male cap attachment (or a similar configured natural male bone joint engaging surface). Also, and with mutual reference to the male cap shaped implant 22, the current variant permits replacement of either the male or female cap shaped implant 46, such as after a given iteration of use, and without requiring concurrent replacement of the base implant component which is secured to the existing reconditioned bone.

Figure 7:
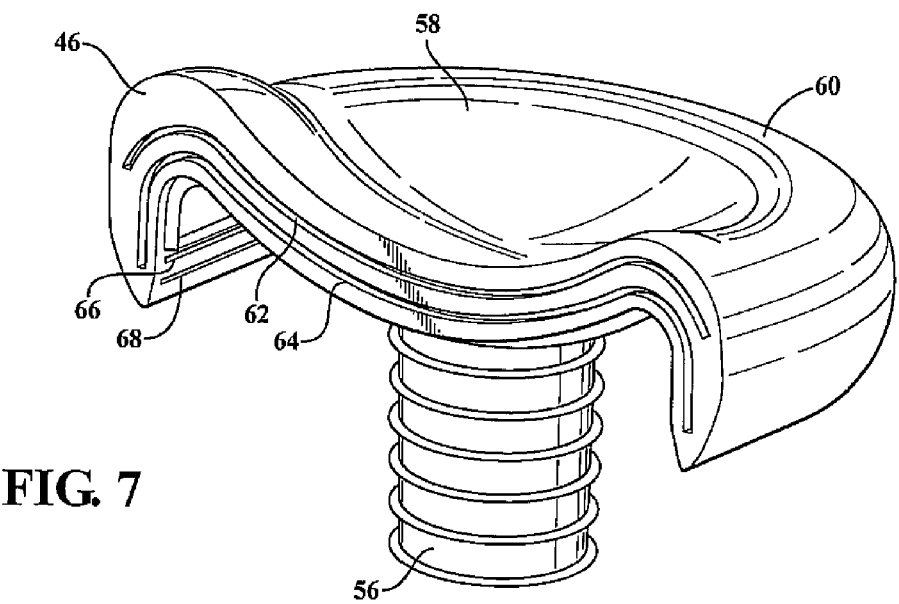
FIG. 7 is a further perspective view of the female partial implant cap of FIG. 6.
Figure 8:
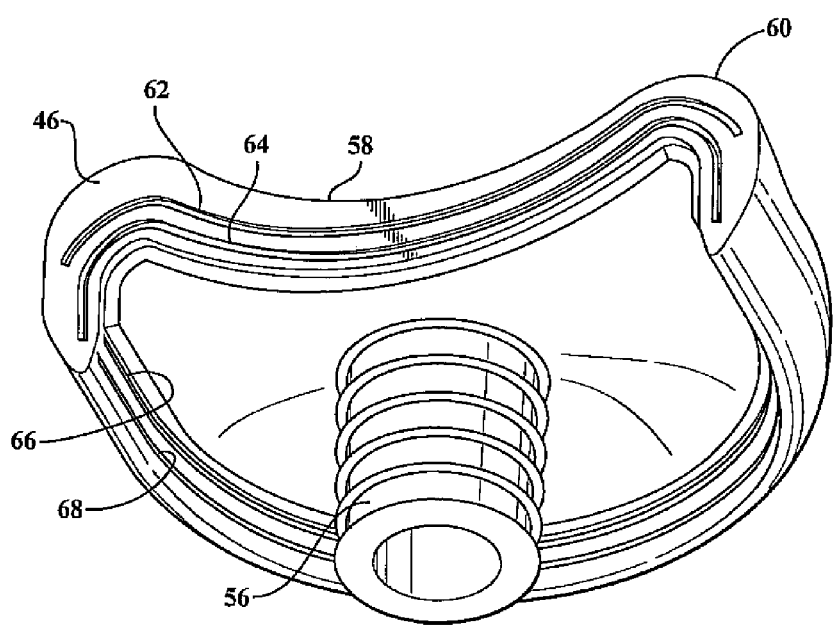
FIG. 8 is a yet further underside facing perspective view of female partial implant cap.

FIG. 6 is a rotated perspective of the female implant assembly of FIG. 5 and again showing a similar threaded mounting shaft for adhesive engagement with a recess defining location of a combined substrate and stem supporting portion of the female (or receiver) joint. Finally, FIGS. 7 and 8 are further perspective views of the female partial implant cap of FIG. 6 and which again can include stiffener inserts (see at 62, 64 and 66, 68) incorporated into the top and base perimeter walls of the cap shaped insert 46 and in order to adjust the material and flexural properties of the cap attachment.

Having described my invention, other and additional preferred embodiments will become apparent to those skilled in the art to which it pertains, and without deviating from the scope of the appended claims:

I claim:

1. A joint implant assembly, comprising:
a first component having a first supporting stem adapted to being mounted to a reconditioned end of a first joint defining bone and having an exposed portion exhibiting a first depth extending aperture;
a first cap attachment exhibiting a convex exterior surface, said first cap attachment having a first underside mating with said first exposed portion, a first screw portion extending from said first underside of said first cap attachment and engaging within said first depth extending aperture for mounting said first cap attachment to said first component; and
a second component having a second supporting stem adapted to being mounted to a reconditioned end of a second joint defining bone and having a second exposed portion exhibiting a second depth extending aperture;
a second cap attachment exhibiting a concave exterior surface, said second cap attachment having a second underside mating with said second exposed portion of said second component, a second screw portion extending from said underside of said second cap attachment and engaging within said second underside depth extending aperture for mounting said second cap attachment to said second component, said first and second cap attachments defining removeable and replaceable components for providing a reconditioned artificial wear surface; and wherein at least one of said exposed portions further includes a plurality of discontinuous and interconnecting side and top surfaces for receiving and securing said mating underside of said respective first or second cap attachments; and further comprising at least one stiffener insert incorporated into a plasticized construction associated with each of the convex and concave shaped cap attachments, wherein said stiffener inserts each have an arcuate profile and are incorporated into a perimeter formed by each of said interconnecting side and top surfaces defining each of said cap attachments.

* * * * *